(12) United States Patent
Frings et al.

(10) Patent No.: US 8,303,606 B2
(45) Date of Patent: Nov. 6, 2012

(54) DEVICE THAT CAN BE MOUNTED ON A SURGICAL SEWING MACHINE TO FORM AN END-TO-END ANASTOMOSIS BETWEEN TWO HOLLOW ORGANS, SUTURING MACHINE AND PROCESS THEREOF

(75) Inventors: Hermann-Josef Frings, Aachen (DE); Clemens Moll, Aachen (DE); Philipp Moll, Aachen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 457 days.

(21) Appl. No.: 12/514,126

(22) PCT Filed: Nov. 6, 2007

(86) PCT No.: PCT/EP2007/009611
§ 371 (c)(1),
(2), (4) Date: May 8, 2009

(87) PCT Pub. No.: WO2008/055655
PCT Pub. Date: May 15, 2008

(65) Prior Publication Data
US 2009/0234373 A1    Sep. 17, 2009

(30) Foreign Application Priority Data
Nov. 9, 2006 (DE) .......................... 10 2006 053 217

(51) Int. Cl.
*A61B 17/04* (2006.01)
*A61B 17/12* (2006.01)

(52) U.S. Cl. ........................................................ 606/144
(58) Field of Classification Search .......... 606/139–150, 606/153–156
See application file for complete search history.

(56) References Cited

U.S. PATENT DOCUMENTS

| 4,553,961 A | 11/1985 | Pohndorf et al. |
| 4,778,467 A | 10/1988 | Stensaas et al. |
| 5,695,504 A * | 12/1997 | Gifford et al. ................. 606/153 |
| 2003/0045891 A1 | 3/2003 | Yamamoto et al. |

FOREIGN PATENT DOCUMENTS

| DE | 101 16 171 A1 | 10/2002 |
| DE | 102 40 331 | 3/2004 |
| EP | 1 415 597 | 5/2004 |

* cited by examiner

*Primary Examiner* — Melanie Tyson
(74) *Attorney, Agent, or Firm* — McGlew and Tuttle, P.C.

(57) ABSTRACT

A process and a device are provided for forming an end-to-end anastomosis on two hollow organs, which can be attached to a surgical suturing machine with at least one driven needle bar with a thread-carrying needle, a shuttle cooperating with this needle, a needle plate and a holding-down device accommodated by a push rod. A carrier (9) is provided designed as a hollow cylinder and has a longitudinal slot (13) for the edge areas of the two hollow organs. The carrier can be connected by a bracket to the housing shaft of the suturing machine in such a way that its longitudinal axis runs transversely to the path of movement of the needle, and its contact area for the two hollow organs is directed essentially parallel to the plane of the contact surface of the needle plate of the suturing machine.

19 Claims, 5 Drawing Sheets

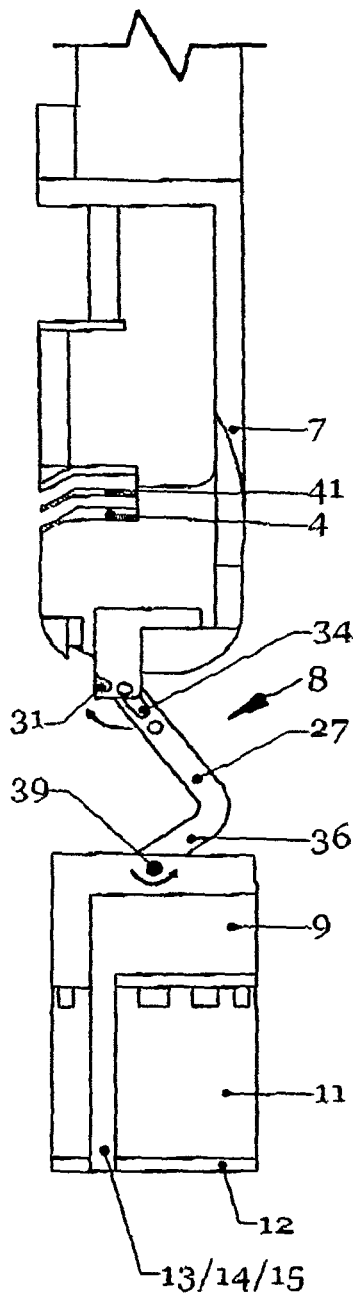
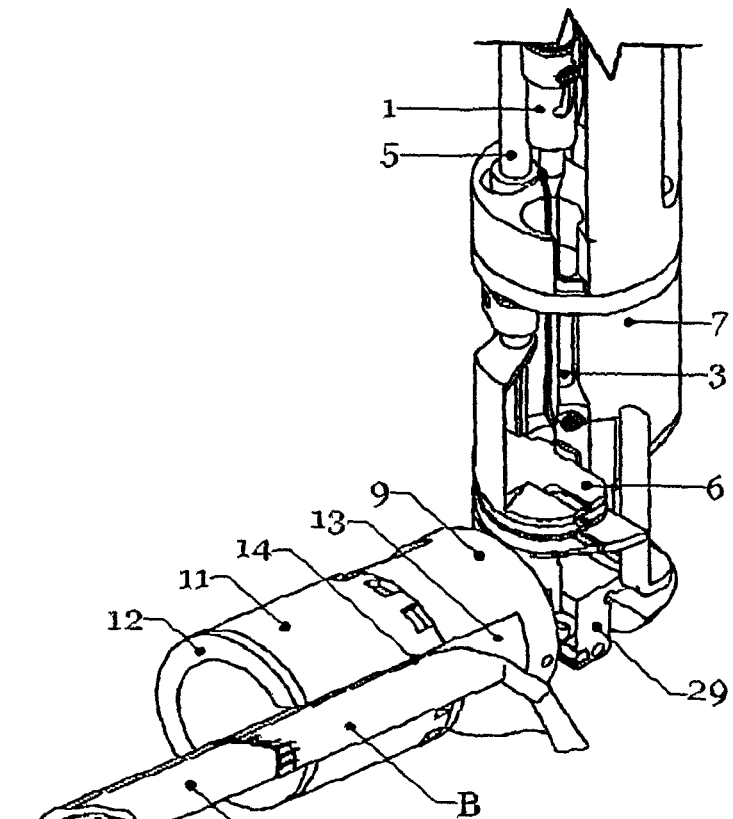
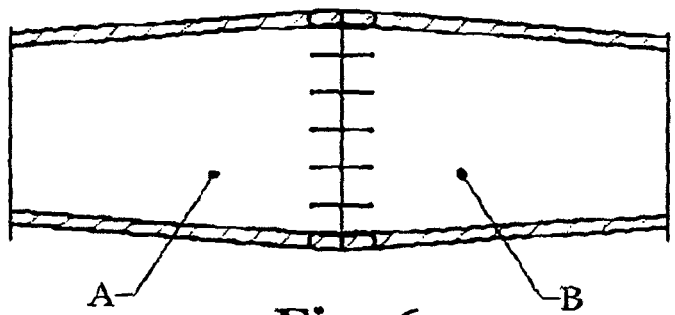
Fig. 9
Fig. 5
Fig. 6

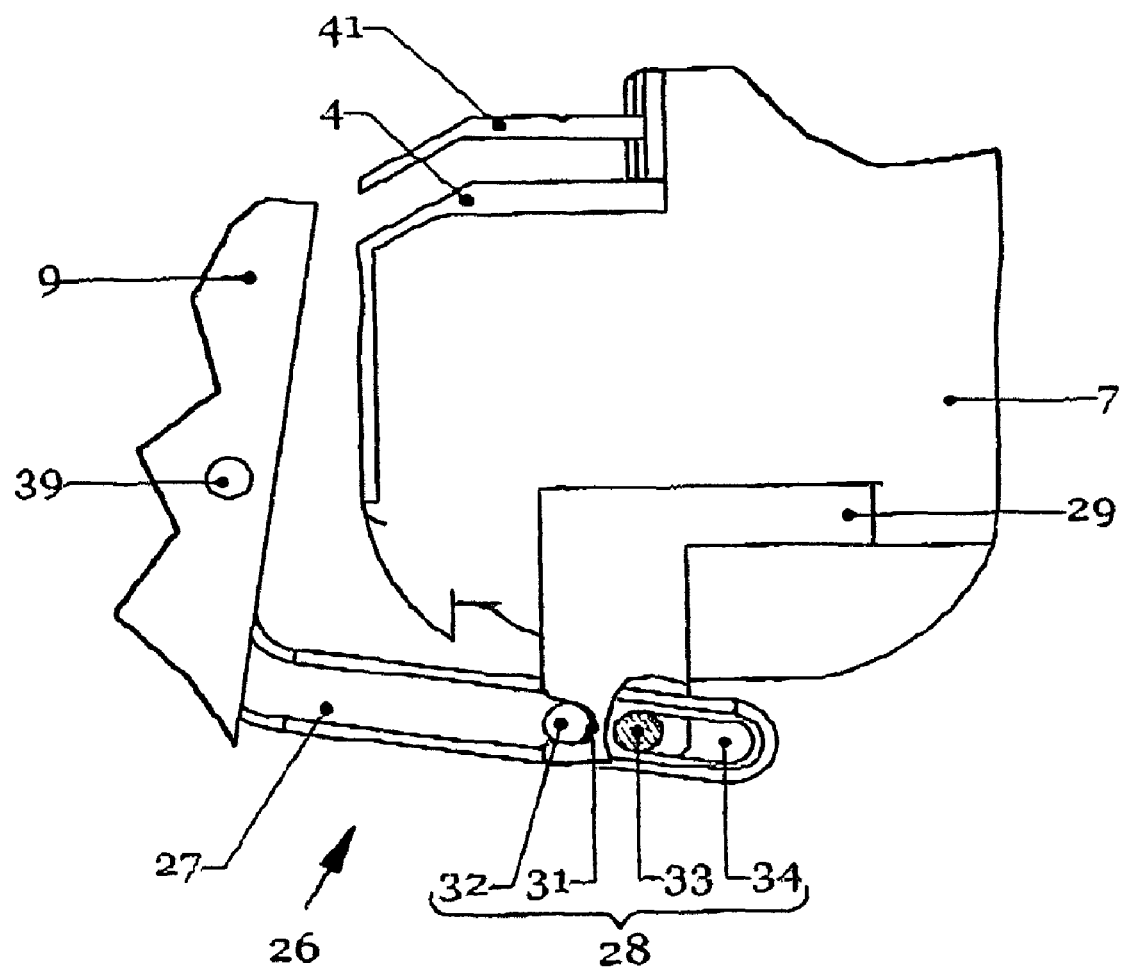

DEVICE THAT CAN BE MOUNTED ON A SURGICAL SEWING MACHINE TO FORM AN END-TO-END ANASTOMOSIS BETWEEN TWO HOLLOW ORGANS, SUTURING MACHINE AND PROCESS THEREOF

CROSS REFERENCE TO RELATED APPLICATIONS

This application is a United States National Phase application of International Application PCT/EP2007/009611 and claims the benefit of priority under 35 U.S.C. §119 of German Patent Application DE 10 2006 053 217.1 filed Nov. 9, 2006, the entire contents of which are incorporated herein by reference.

FIELD OF THE INVENTION

The present invention pertains to a device for forming an end-to-end anastomosis on two hollow organs, which can be attached to a surgical suturing machine with at least one motor-driven needle bar with a thread-carrying needle, a shuttle cooperating with this needle, a needle plate and a holding-down device for the material to be sutured accommodated by a push rod.

BACKGROUND OF THE INVENTION

In medical engineering, it is common in certain diseases of hollow organs, to cut out sick areas of same, for example, sick intestinal areas and to reconnect the two cut ends to each other. Thus, for example, the intestinal end coming from the stomach is sutured at the beginning of the continuing intestinal section.

This is still mainly done by hand, whereby a needle provided with a thread is mounted in a needle holder guided by the physician. For forming the seam, the first lip is hereby held firmly by means of forceps, which is then pierced by the needle in direct vicinity of the forceps. The second lip is then picked up and held firmly with the forceps, which is then likewise pierced in the area of the forceps. This procedure is then repeated so often until the seam is formed along the entire circumference of the intestinal sections, whereby it should be noted that, on the one hand, the two hollow organs are sutured together end to end, and, on the other hand, the inner mucosa does not penetrate outwards.

This type of stitch formation corresponds essentially to the type of formation of a common manual seam of a seamstress or a tailor, whereby the quality of the seam depends primarily on the attention and especially on the skillfulness of the needle guiding by the physician.

A surgical suturing machine, designed as an endoscopic suturing machine, which has a housing that is formed from a housing upper part and a housing shaft adjacent thereto, has become known from DE 101 16 171 A1. The housing upper part here is primarily used for receiving drives for the stitch-forming tools, while the housing shaft is used for receiving means for transmitting the movements generated by the drives to the stitch-forming tools, which means have a thread-carrying needle accommodated by a needle bar and a shuttle cooperating with this needle.

Further, both a needle plate and a holding-down device, which is driven by a drive provided in the housing upper part and is accommodated by a pushing means, is arranged in the area of the lower end of the housing shaft.

For forming a seam, the shuttle is moved, after grasping the thread loop formed by the needle, along a multidimensional path of movement from a position located under the material to be sutured and grasping the thread loop into a position located above the material to be sutured, in which the thread triangle formed by the thread loop guided into the upper side of the material to be sutured encloses the projection of the needle path.

In this way—as shown in FIGS. 8 through 12 of DE 101 16 171 A1—it is possible to form a cover seam using a stitch type corresponding to the stitch type 501.

Thus, this endoscopic suturing machine is suitable for connecting lips, which lie flat on each other or next to each other, to each other by means of a seam of the above-described type and thus for replacing the manual seam formation; however, this endoscopic suturing machine is not provided for forming end-to-end anastomoses on two hollow organs and hence is not optimal.

SUMMARY OF THE INVENTION

Therefore, the basic object of the present invention is to provide a device, which, on the one hand, makes possible the formation of end-to-end anastomoses on two hollow organs, but, on the other hand, engages in the structure of the prior-art surgical suturing machine as little as possible. Thus, the further basic object of the present invention is to provide a device, which makes possible an "all-round suturing" at the two hollow organs to be connected in their essentially cylindrical state; however, at the same time it is guaranteed that the insides and outsides of the hollow organs are not mixed up.

This object is accomplished by a device that can be attached to an above-described surgical suturing machine with a carrier, which is designed as a hollow cylinder and has a longitudinal slot, for the edge zones of the two hollow organs to be connected to one another, which can be connected to the housing of the suturing machine by means of a bracket in such a way that its longitudinal axis runs transversely to the path of movement of the needle of the suturing machine, and its contact area for the two hollow organs is directed essentially parallel to the plane of the contact surface of the needle plate of the suturing machine.

Consequently, it is possible to introduce the first hollow organ into the carrier in such a way that its edge area protrudes opposite the carrier by a defined amount and the protruding edge area can be pulled back over the carrier in such a way that the outside of the hollow organ lies on or rests on the outside of the carrier, whereby the edge zone of the hollow organ is located under the needle and it rests on the needle plate. Then, the edge area of the second hollow organ can be pushed so far onto the pulled-back area of the first hollow organ until its edge zone is likewise located under the needle and marginally equal to the edge zone of the first hollow organ and rests with its inside on the inside of the first hollow organ. In this position of the two hollow organs, the seam connecting the edge areas of the two hollow organs can be formed by means of the surgical suturing machine within the edge zones of the two hollow organs. The two hollow organs are to be moved further under the removed needle at the end of each stitch formation each time by an amount corresponding to the stitch length of the seam. After completion of the seam, the two hollow organs, which have their essentially cylindrical shape during the suturing, may be pressed somewhat flat in the short term, so that the first hollow organ can be moved out of the carrier through the longitudinal slot provided in the carrier and can be brought into a stretched position.

In another embodiment of the present invention, a sleeve, which is arranged coaxially to the carrier and is rotatable in relation to same, is provided, whose jacket surface is used as a contact surface for the edge areas of the two hollow organs, and the sleeve likewise has a longitudinal slot extending at least over a part of its length.

Since the sleeve is mounted directly on the carrier and thus is rotatable about a full 360°, the seam to be made can be made within these 360° and thus with a rotation of the sleeve, whereby it should only be noted that, on the one hand, the edge areas of the two hollow organs, lying one above the other, always assume their proper position in the area of the stitch-forming site, and, on the other hand, the sleeve is further rotated by the corresponding angular amount after each stitch formation.

In order to guarantee a constantly equal stitch length, the sleeve can be motor driven in relation to the carrier, whereby the movement of the drive of the sleeve is diverted by the drive of the suturing machine in such a way that the sleeve makes an intermittent rotary movement in a phased manner for the formation of a seam depending on the movement of the needle bar or of the push rod, as a result of which not only is a constantly equal stitch length achieved, but it is also guaranteed that the rotary movement of the sleeve is always made in a phased manner to same in relation to the stitch formation.

A structurally simple solution for the diversion of the rotary movement of the sleeve by the drive of the suturing machine arises when the sleeve has teeth on one of its faces, with which a driving pawl mounted at the carrier cooperates, which can be connected to the drive of the needle bar or of the push rod in a driven manner by means of a deformable transmission means.

It is advantageous here if the transmission means is a chain or a Bowden cable, whose one end can be connected to the drive of the needle bar or of the push rod, and whose other end acts on a lever accommodating the driving pawl, which lever is pivotably mounted at the carrier, whereby the driving pawl is held in a position of not meshing with the teeth of the sleeve by means of a spring.

To achieve the diversion of the movement of the sleeve by the pivoting movement of the driving pawl, it is advantageous if this driving pawl is arranged off-center to the sleeve and meshes with its teeth in a nonpositive manner, such that a phased, intermittent rotary movement of the sleeve can be diverted by the pivoting movements of the driving pawl.

With the solution according to the present invention, it is desired not to interfere with the structure and function of the surgical suturing machine described in the introduction and hence to make this attachable to the surgical suturing machine, whereby at the same time an as compact as possible shape of the device in the nonuse position shall be guaranteed.

This is advantageously achieved in that the bracket for the carrier is formed by an angular carrying piece, whose first arm can be connected via a first lockable hinge connection to a spacer fastened to the house of the surgical suturing machine, and whose second arm can be connected to the carrier by means of a second, likewise lockable hinge connection, and the bracket can be moved from the position securing the operating position of the carrier into a position, in which the carrier is directed essentially parallel to the longitudinal axis of the suturing machine.

Since the distance between the contact points of the Bowden cable at the needle bar or at the push rod and the lever for the driving pawl in the operating position of the carrier is different from the distance between the contact points of the Bowden cable in the inoperative position of the carrier, the Bowden cable is routed via a plurality of deflections, of which at least one is arranged at the carrier and another is arranged at the first arm of the bracket or at the housing shaft of the surgical suturing machine.

Other advantages and details of the present invention arise based on the following description of an exemplary embodiment of the present invention shown in the attached drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a schematic perspective view of the device according to the present invention after the suturing procedure during the removal of the hollow organs A, B;

FIG. 6 is a top sectional view of the hollow organs A, B connected to each other by an all-round seam;

FIG. 9 is a front view of the device according to the present invention in the insertion position with the housing shaft of the suturing machine; and FIG. 10 is an enlarged view of the locked position of the first arm of the carrying piece with the housing shaft of the suturing machine.

DESCRIPTION OF THE PREFERRED EMBODIMENTS

Figure 3:
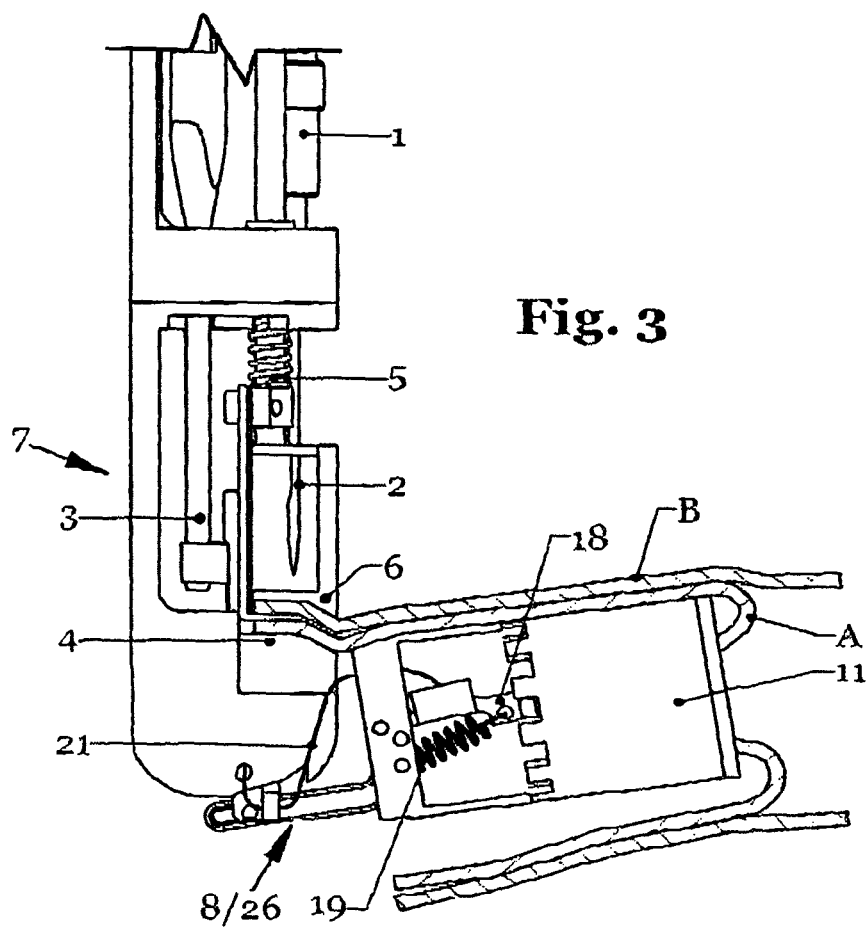
FIG. 3 is a schematic view showing the lower area of the suturing machine with a device according to the present invention attached thereto with hollow organs located in the suturing position.
Figure 4:
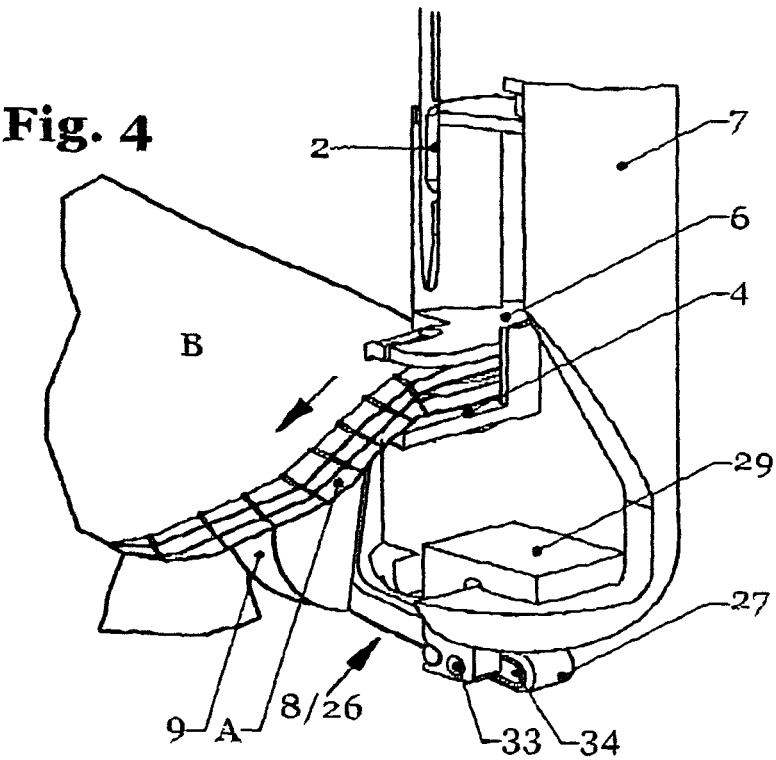
FIG. 4 is a schematic perspective view of the device according to the present invention during the suturing procedure.

Referring to the drawings in particular, the lower area of a surgical suturing machine, as it is shown and described, for example, in DE 101 16 171 A1 or EP 1 372 490 B1, is shown in FIG. 3.

This suturing machine has a motor driven needle bar 1 along with a thread-carrying needle 2, which cooperates with a shuttle to form a chain stitch seam of the stitch type 501 or a stitch type similar hereto. The stitch formation, which is not of further interest in detail here, is shown in FIGS. 8 through 12 of the above-mentioned publications and is also explained in detail in the specification.

Besides the needle 2 and the (not shown) shuttle attached to a shuttle bar 3, the suturing machine has a needle plate 4 with a slot-like stitch hole and a holding-down device 6 accommodated by a push rod 5, likewise provided with a slot, for the hollow organs A, B, which holding-down device is periodically raised depending on the movement of the needle 2 to facilitate the feed movement of the two hollow organs A, B during the removed phases of the needle 2.

In the exemplary embodiment of the present invention shown, in the lower area of the housing shaft 7 of the surgical suturing machine according to DE 101 16 171 A1 or EP 1 372 490 B1 is provided a bracket 8, which can be detachably connected to same, for a carrier 9 that is designed as a hollow cylinder, on which a sleeve 11 is rotatably mounted, whereby a clamping ring 12 is arranged on one of the faces of the sleeve 11.

The jacket surface of the sleeve 11 is used as a contact surface for the edge areas of the two hollow organs A, B to be connected to each other. The carrier 9 and sleeve 11 are arranged in relation to the suturing machine in such a way that their longitudinal axes run transverse to the path of movement of the needle 2 of the suturing machine. Furthermore, the carrier 9 and the sleeve 11 are arranged in such a way that the contact area of the sleeve for the two hollow organs A, B is directed essentially parallel, but preferably at an acute angle to the plane of the contact surface of the needle plate 4 of the suturing machine. The carrier 9 and sleeve 11 have a longitudinal slot 13 and 14, respectively, each for a purpose to be explained later, which slot extends over at least a part of the length of the carrier 9 or of the sleeve 11, respectively. The relative position between the carrier 9 and the sleeve 11 can be adjusted by rotating the sleeve 11 in such a way that the two longitudinal slots 13, 14 run congruent to one another. The clamping ring 12 is also provided with a corresponding longitudinal slot 15, which corresponds to the longitudinal slot 14 provided in the sleeve 11. The clamping ring 12 is therefore inserted into the sleeve 11 in such a way that the two longitudinal slots 14, 15 run congruent to one another.

Figure 1:
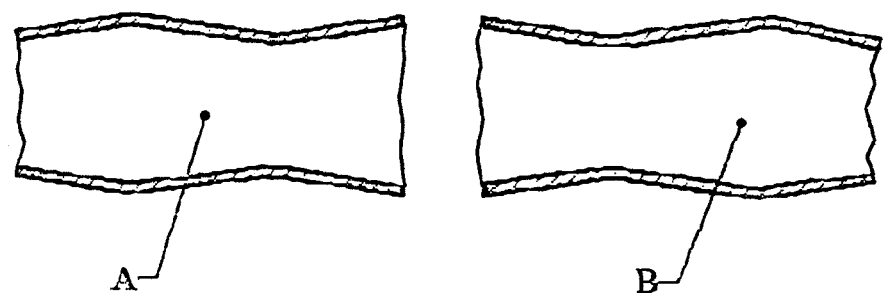
FIG. 1 is a sectional view showing the two hollow organs A, B to be connected to each other.
Figure 2:
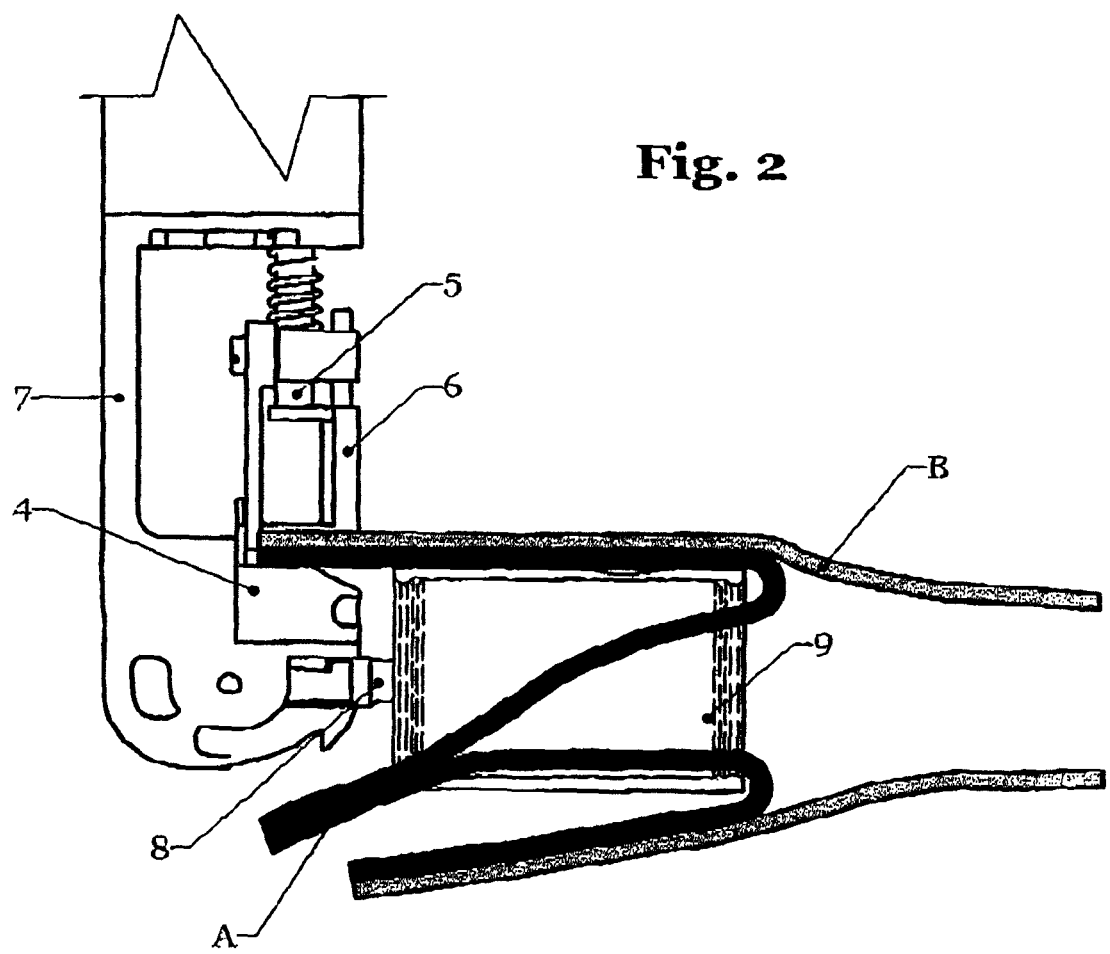
FIG. 2 is a schematic view of the lower area of a surgical suturing machine according to DE 101 16 171 A1 with the hollow organs prepared for the suturing procedure.

FIG. 1 shows the edge areas of two hollow organs A, B having an essentially cylindrical shape, which shall be connected by means of a seam at their edge zones which are adjacent to each other.

Starting from here, the free end of the hollow organ A is inserted into the carrier 9 or the sleeve 11 in such a way that its edge area protrudes opposite the carrier 9 or sleeve 11 by a defined amount, so that the protruding edge area can be pulled back over the sleeve 11 in such a way that the outside of the hollow organ A lies or rests on the outside of the sleeve, whereby the edge zone of the edge area of the hollow organ A is located under the needle 2 of the surgical suturing machine and rests on its needle plate 4.

Then, the edge area of the hollow organ B can be pushed so far onto the pulled-back area of the hollow organ A until its edge zone is also located congruently to the edge zone of the hollow organ A under the needle 2 and rests with its inside on the inside of the hollow organ A pulled outwards.

In this position of the two hollow organs A, B, a seam connecting same to one another can be formed by means of the surgical suturing machine within the edge zones of the two edge areas of the hollow organs A, B. The seam may be, for example, a single-thread cover seam of stitch type 501, whose formation is shown and described in FIGS. 8 through 12 of DE 101 16 171 A1 or EP 1 372 490 B1. In this stitch type, the thread loop formed on the underside of the material to be sutured is guided by the shuttle from the underside of the material to be sutured to its upper side and is then continuously fixed there by the needle piercing the thread loop. This stitch type is especially quite suitable for the present purpose since the connected walls of the two hollow organs, lying one above the other, can very easily be brought into a stretched position shown in FIG. 6.

For continuous stitch formation and thus for the formation of all-round seam, the two hollow organs A, B must be further moved in a phased manner for the stitch formation at the end of each stitch formation by means of successive rotation of the sleeve 11 each time by an amount corresponding to the stitch length of the seam with the needle 2 removed until the seam beginning is reached and thus the all-round seam is formed. After completion of the seam, the two hollow organs A, B connected to one another by the seam, which have their essentially cylindrical shape during the suturing, are at first moved away so far from the stitch-forming site of the surgical suturing machine until their edge areas provided with the seam are located in the area of the longitudinal slots 13, 14 of the carrier 9 and the sleeve 11. After the longitudinal slots 13, 14 are brought into a congruent position by rotating the sleeve 11, the hollow organs A, B are pressed somewhat flat in the short term, so that the hollow organ A can be moved out of the sleeve 11 or the carrier 9 by means of the longitudinal slots 13, 14 provided in the carrier 9 or sleeve 11, and both hollow organs A, B can be brought into a stretched position, in which they assume the position shown in FIG. 6.

In a preferred embodiment, the device according to the present invention is provided with a rotary drive for the sleeve 11, whose driving movement is reduced by the stroke movement of the needle bar 2 or of the push bar 5 of the holding-down device 6 of the surgical suturing machine, so that the sleeve 11 performs a phased, intermittent rotary movement for the stitch formation.

For this purpose, on the face of the sleeve 11 (FIG. 8) facing away from the clamping ring 12 are provided teeth 16, with which a driving pawl 17 cooperates, which pawl is provided on a lever 18 pivotably mounted at the carrier 9 by means of a pin 20. The driving pawl 17 is held in a position of not meshing with the teeth 16 of the sleeve 11 by means of a spring 19 acting on the lever 18 at one end and acting on the carrier 9 at the other end. A deformable transmission means designed as a Bowden cable 21 in the exemplary embodiment acts on the lever 18, whose other end is connected to the push rod 5 for the holding-down device 6. For this purpose, the Bowden cable is guided both via a first guide 22 attached at the carrier 9 and via a second guide 23 arranged at the housing shaft 7 of the surgical suturing machine. Thus, during the stroke movement of the holding-down device 6, the driving pawl 17 is at the same time raised with this device.

The driving pawl 17 is arranged off-center to the sleeve 11 and lies in a nonpositive manner during its pivoting movement introduced by the Bowden cable 21 on the underside of a tooth of the teeth 16 of the sleeve 11. Consequently, an essentially tangentially directed force component is derived from its pivoting or stroke movement, which brings about rotary movement of the sleeve 11, which consequently occurs in a phased manner for the stroke movement of the push rod 5 of the holding-down device 6. Since the driving pawl 17 lies on the underside of the teeth 16 in a nonpositive manner, and the respective tooth is moved away during the rotary movement of the sleeve 11 via the driving pawl 17, the driving pawl 17 becomes unmeshed without additional control means after a rotary movement of the sleeve 11 corresponding to the width of the respective tooth and is then returned into its inoperative position by means of the spring 19. In order to counteract an unwanted movement of the sleeve during the inserted phase of the needle, a brake 24, which is designed as a spiral spring, is provided at the carrier 9, which brake lies on the inside of the teeth 16.

In a preferred embodiment, the Bowden cable 21 does not act directly on the lever 18, but rather on a sliding piece 25, which can be shifted and fixed on this lever, so that the extent of the pivoting movement of the driving pawl 17 or its pressing force onto the teeth can be adjusted within defined limits, so that the extent of the respective rotary movement of the sleeve 11 and thus the stitch length of the seam to be formed can also be adjusted within corresponding limits.

Figure 7:
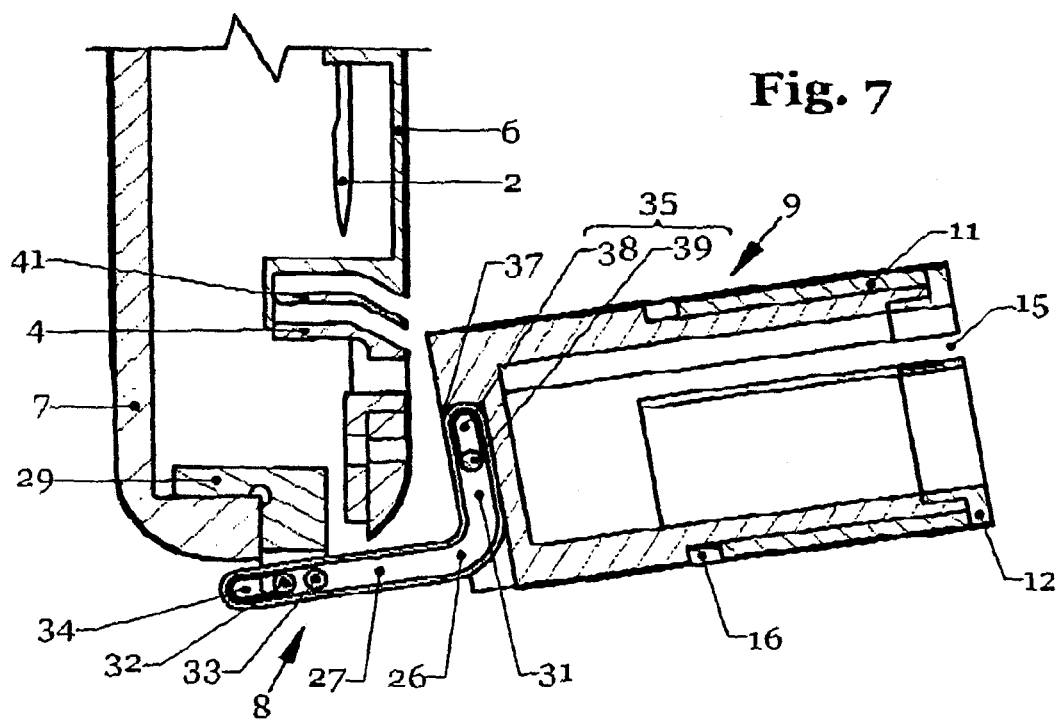
FIG. 7 is a longitudinal sectional view of the carrier with its bracket and the housing shaft of the suturing machine.
Figure 8:
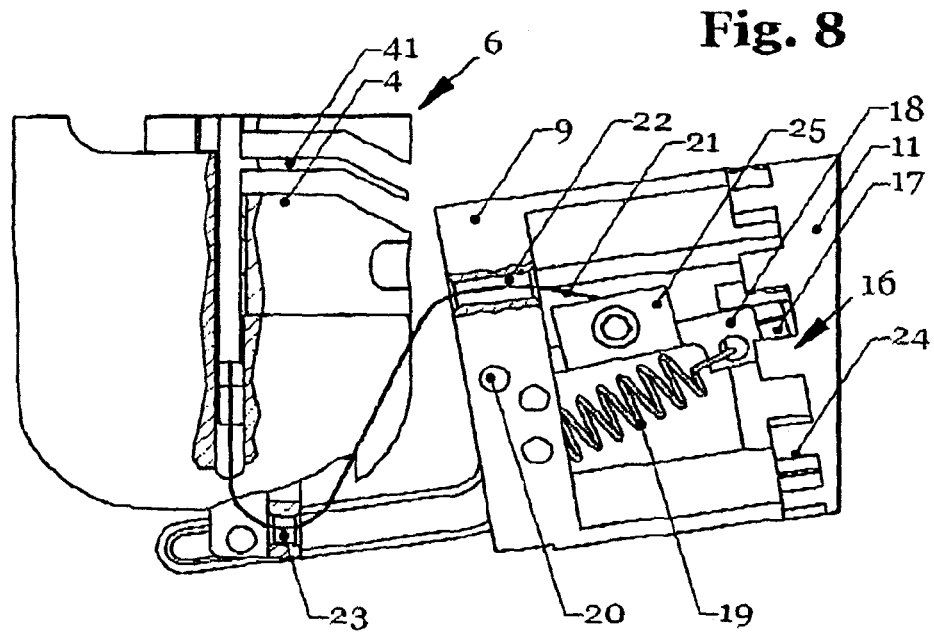
FIG. 8 is a partial sectional view of the carrier and of the sleeve with its drive and the housing shaft of the suturing machine.

For connecting the carrier 9 to the housing shaft 7 of the surgical suturing machine, the bracket 8 comprises an angular carrying piece 26 (FIG. 7), whose first arm 27 can be connected by means of a first lockable hinge connection 28 to a spacer 29 fastened to the housing shaft 7 of the surgical suturing machine, and whose second arm 31 can be connected to the carrier 9 by means of a second, likewise lockable hinge connection 32.

Here, the first hinge connection 28 between the first arm 27 of the carrying piece 26 and the spacer 29 comprises a locking opening, which is provided at this spacer and is open on one side, into which protrudes a pin 32 arranged in the arm 27 of the carrying piece 26 and can be locked in same. A mounting pin 33 running parallel to the pin 32 is fastened to the spacer 26, which mounting pin meshes with a longitudinal hole provided in the arm 27 of the bracket. This relative position of the arm 27 of the angular carrying piece 26 or of the bracket 8, which is secured by means of the pin 32 locked in the locking opening 31 and the mounting pin 33 protruding into the longitudinal hole 34 of the arm 27, corresponds to the operating position of the carrier 9 or of the sleeve 11.

For pivoting the bracket 8, its arm 27 is first moved so far away from the spacer 29 that the pin 32 becomes unmeshed from the locking opening 31. During this movement, the mounting pin 32 slides to the other end of the longitudinal hole 34 and in this position forms a pivoting axis for the arm 27 or the carrying piece 26, so that same makes a pivoting movement of ca. 90° about the mounting pin 33.

For forming the hinge connection 35 between the second arm 36 of the carrying piece 26 and the carrier 9, a recess 37 corresponding to the shape of the second arm 36 is provided on its face, with which the second arm 36 meshes. In the area of the free end of the arm 36 is provided a longitudinal hole 38, with which a mounting pin 39 fastened in the carrier 9 meshes. In the operating position of the carrier 9, the mounting pin 39 is located in the area of the—with reference to FIG. 7— lower end of the longitudinal hole 38 and moves towards the upper end of the longitudinal hole 38 during the pivoting movement of the carrying piece 26 about the mounting pin 33. In this position of the mounting pin 39, this is used as the pivoting axis for the carrier 9, so that same can be pivoted into a position that is essentially in alignment with the longitudinal axis of the suturing machine, which is shown in FIG. 9.

In a preferred variant of the embodiment of the device, above the needle plate 4 there is provided an intermediate plate 41, running essentially parallel thereto, which is slightly beveled in its front area. Consequently, it is possible to place the outside of the edge area of the hollow organ A onto the needle plate 4 and the inside of the edge area of the hollow organ B onto the intermediate plate 41, so that it is guaranteed that the two insides of the two hollow organs A, B do not lie on one another directly in the area of the holding-down device 6. Consequently, it is ruled out that the insides of the two hollow organs A, B are thus pressed directly against one another by pressing the holding-down device 6.

In this case, the intermediate plate 41 can be guided by means of a guide (not shown) provided on the holding-down device 6 parallel to this device, and can be held at an elevated distance from the needle plate 4 to facilitate the insertion of the edge areas of the two hollow organs A, B in the raised position of the holding-down device 6.

In another embodiment of the present invention, instead of the cylinder-shaped carrier with the sleeve arranged coaxially thereto, an essentially rod-shaped or half-shell-shaped carrier can also be used, on whose two longitudinal sides a flat or arc-shaped support part each is connected, whereby the respective contact surface of the arc-shaped support part can have a concave or convex shape.

In this case, the rod-shaped or half-shell-shaped carrier can be connected to the second arm of the carrying piece in such a way that a corresponding movement of the respective two support parts can be derived from the pivoting movement guiding it from the inoperative position into its operating position or from its operating position into its inoperative position in such a way that these support parts are moved from their expanded operating position into a folded-up position, in which they are essentially aligned with the longitudinal axis of the surgical suturing machine, during the pivoting movement of the carrier from the inoperative position into its operating position into its expanded position during the pivoting movement guiding it from its operating position into its inoperative position.

This embodiment is especially advantageous when a seam shall be formed on larger organs and the organs to be connected shall be held at a defined relative position to the areas to be sutured during the seam formation.

In the area of surgery, besides the connecting technique of "suturing by means of threads," still such other connecting techniques as, for example, "clamping" are well known, which are used both in laparoscopic and open surgery.

The device according to the present invention and the process based on same were explained above using the example of suturing; however, the use of the teaching according to the present invention is not limited to suturing. Rather, this may also be easily used during clamping in view of the fact that, both when suturing and when clamping, the actual connecting means (threads or clamps) are guided in both techniques from one side of the lips to the other side, whereby, when suturing, the seam is secured by repeated looping of the thread, while, when clamping, the fixed seating of the clamps is achieved by bending the free ends of the clamps.

It is likewise possible to make the connection of the two lips by using the teaching according to the present invention by laser welding with the aid of corresponding welding aids.

While specific embodiments of the invention have been described in detail to illustrate the application of the principles of the invention, it will be understood that the invention may be embodied otherwise without departing from such principles.

The invention claimed is:

1. A device for forming an end-to-end anastomisis on two hollow organs, which can be attached to a suturing machine with at least one motor driven needle bar with a thread-carrying needle, a shuttle cooperating with same, a needle plate, and a holding-down device for the material to be sutured accommodated by a push rod, the device comprising:
   a carrier comprising a hollow cylinder having a longitudinal axis that is configured to extend at an acute angle to the contact surface of the needle plate of the suturing machine and having a longitudinal slot for edge areas of the two hollow organs to be connected to one another;
   a bracket for connecting said carrier to the a housing shaft of the suturing machine in such a way that a longitudinal axis of said carrier runs transversely to the path of movement of the needle of the suturing machine, and a contact area for the two hollow organs is directed essentially parallel to the plane of the contact surface of the needle plate of the suturing machine;
   a sleeve, which is arranged coaxially to said carrier and can be rotated in relation to said carrier, said sleeve having a jacket surface used as a contact surface for the end areas of the two hollow organs, and said sleeve having a sleeve longitudinal slot extending over at least a part of a length thereof;

a clamping ring wherein said sleeve has faces and can be closed on one of said faces by means of said clamping ring, said clamping ring having a longitudinal slot corresponding to said sleeve longitudinal slot; and a sleeve drive, said sleeve being rotatable in relation to said carrier by means of said sleeve drive, and movement of said sleeve drive of said sleeve is diverted by the drive of the suturing machine in such a way that said sleeve makes an intermittent rotary movement in a phased manner depending on the movement of the needle bar or a push rod for the formation of a seam.

2. A device attachable to a surgical suturing machine in accordance with claim 1, further comprising:

a deformable transmission means; and a driving pawl mounted at said carrier, wherin at an end facing away from said clamping ring, said sleeve has teeth with which said driving pawl cooperates, said driving pawl being connected to the drive of the needle bar or the push rod in a driven manner by means of said deformable transmission means.

3. A device attachable to a surgical suturing machine in accordance with claim 2, wherein said driving pawl is arranged off-center to said sleeve and meshes in a nonpositive manner with an inside of said teeth.

4. A device attachable to a surgical suturing machine in accordance with claim 2, further comprising a lever accommodating said driving pawl, said lever being pivotably mounted at said carrier wherein said deformable transmission means is a Bowden cable with an end to be connected to the drive of the needle bar or of the push rod, and with another end acting upon said lever accommodating said driving pawl, which is pivotably mounted at said carrier.

5. A device attachable to a surgical suturing machine in accordance with claim 4, further comprising a spring wherein said driving pawl is held in a position of not meshing with said teeth of said sleeve by said spring.

6. A device attachable to a surgical suturing machine in accordance with claim 4, further comprising a plurality of deflections wherin said Bowden cable is routed via said plurality of deflections, one of said a plurality of deflections being arranged at said carrier and another of said a plurality of deflections being arranged at a first arm of a carrying piece of said bracket or at the housing shaft.

7. A device attachable to a surgical suturing machine in accordance with claim 1, further comprising:

a first hinge connection; and a second hinge connection, wherein said bracket comprises an angular carrying piece with a first arm connected by said first hinge connection to a spacer fastened at the housing of the surgical suturing machine, and with a second arm connected to said carrier by means of said second hinge connection, said bracket moving from a position securing an operating position of said carrier into a position in which said carrier is directed essentially parallel to the longitudinal axis of the suturing machine.

8. A device attachable to a surgical suturing machine in accordance with claim 7, wherein said first hinge connection and said second hinge connection are lockable.

9. A device attachable to a surgical suturing machine in accordance with claim 8, wherein said first hinge connection is detachably connected to the spacer of the housing shaft of the surgical suturing machine.

10. A surgical suturing machine in combination with a device for forming an end-to-end anastomosis, the combination comprising:

the surgical suturing machine comprising:

a motor driven needle bar with a thread-carrying needle and a suturing machine drive;

a shuttle cooperating with said needle bar;

a needle plate; and a holding-down device for the material to be sutured accommodated by a push rod; and the device comprising:

a carrier comprising a hollow cylinder having a longitudinal axis that extends at an acute angle to the contact surface of the needle plate of the suturing machine and having a longitudinal slot for edge areas of the two hollow organs to be connected to one another;

a bracket for connecting said carrier to the housing shaft of the suturing machine in such a way that a longitudinal axis of said carrier runs transversely to the path of movement of the needle of the suturing machine, and a contact area for the two hollow organs is directed essentially parallel to the plane of the contact surface of the needle plate of the suturing machine;

a sleeve, which is arranged coaxially to said carrier and can be rotated in relation to said carrier, said sleeve having a jacket surface used as a contact surface for the end areas of the two hollow organs, and said sleeve having a sleeve longitudinal slot extending over at least a part of a length thereof;

a clamping ring wherein said sleeve has faces and can be closed on one of said faces by means of said claiming ring, said clamping ring having a longitudinal slot corresponding to said sleeve longitudinal slot; and a sleeve drive, said sleeve being rotatable in relation to said carrier by means of said sleeve drive, and movement of said sleeve drive is diverted by said suturing machine drive in such a way that said sleeve makes an intermittent rotary movement in a phased manner depending on the movement of the needle bar or a push rod for the formation of a seam.

11. A combination in accordance with claim 10, further comprising:

a deformable transmission means; and a driving pawl mounted at said carrier, wherin at an end facing away from said clamping ring, said sleeve has teeth with which said driving pawl cooperates, said driving pawl being connected to the drive of the needle bar or the push rod in a driven manner by means of said deformable transmission means.

12. A combination in accordance with claim 11, wherein said driving pawl is arranged off-center to said sleeve and meshes in a nonpositive manner with an inside of said teeth.

13. A combination in accordance with claim 11, further comprising a lever accommodating said driving pawl, said lever being pivotably mounted at said carrier wherein said deformable transmission means is a Bowden cable with an end to be connected to the drive of the needle bar or of the push rod, and with another end acting upon said lever accommodating said driving pawl, which is pivotably mounted at said carrier.

14. A combination in accordance with claim 13, further comprising a spring wherein said driving pawl is held in a position of not meshing with said teeth of said sleeve by said spring.

15. A combination in accordance with claim 13, further comprising a plurality of deflections wherein said Bowden cable is routed via said plurality of deflections, one of said a plurality of deflections being arranged at said carrier and another of said a plurality of deflections being arranged at a first arm of a carrying piece of said bracket or at the housing shaft.

16. A combination in accordance with claim 10, further comprising:
   a first hinge connection; and
   a second hinge connection, wherein said bracket comprises an angular carrying piece with a first arm connected by said first hinge connection to a spacer fastened at the housing of the surgical suturing machine, and with a second arm connected to said carrier by means of said second hinge connection, said bracket moving from a position securing an operating position of said carrier into a position in which said carrier is directed essentially parallel to the longitudinal axis of the suturing machine.

17. A combination in accordance with claim 16, wherein said first hinge connection and said second hinge connection ar lockable.

18. A combination in accordance with claim 17, wherein said first hinge connection is detachably connected to the spacer or the housing shaft of the surgical suturing machine.

19. A combination in accordance with claim 10, wherein above the needle plate an intermediate plate running essentially parallel to same is provided with a contact surface for the above-lying hollow organ during the suturing procedure.

* * * * *